United States Patent [19]

Richmond et al.

[11] Patent Number: 5,504,332

[45] Date of Patent: Apr. 2, 1996

[54] METHOD AND SYSTEM FOR DETERMINING THE HOMOGENEITY OF TABLETS

[75] Inventors: Eric W. Richmond, North Wales; Bruce R. Buchanan, Perkiomenville; Mark A. Baxter, Lansdale; Andy Duff, Lansdale; Oksana M. Tully, Lansdale; Samuel A. Thornton, Lansdale, all of Pa.

[73] Assignee: Merck & Co., Inc., Rahway, N.J.

[21] Appl. No.: 296,833

[22] Filed: Aug. 26, 1994

[51] Int. Cl.$^6$ .......................... G01N 21/17; G01N 21/25
[52] U.S. Cl. ................ 250/339.12; 250/339.11; 250/341.8
[58] Field of Search ............... 250/339.11, 339.12, 250/341.8, 340

[56] References Cited

U.S. PATENT DOCUMENTS

| | | | |
|---|---|---|---|
| 2,650,307 | 8/1953 | Koppius | 250/43.5 |
| 4,640,614 | 2/1987 | Roberts et al. | 356/36 |
| 4,742,228 | 5/1988 | Bischoff | 250/910 X |
| 4,883,963 | 11/1989 | Kemeny et al. | 250/339.11 |
| 4,963,745 | 10/1990 | Maggard | 250/343 |
| 4,975,581 | 12/1990 | Robinson et al. | 250/339 |
| 5,046,846 | 9/1991 | Ray et al. | 250/339.12 |
| 5,099,123 | 3/1992 | Harjunmaa | 250/345 |
| 5,145,785 | 9/1992 | Maggard et al. | 436/8 |
| 5,187,368 | 2/1993 | Galante et al. | 250/341 |
| 5,223,714 | 6/1993 | Maggard | 250/343 |
| 5,223,715 | 6/1993 | Taylor | 250/343 |
| 5,305,076 | 4/1994 | Inoue et al. | 356/346 |
| 5,406,084 | 4/1995 | Tobler et al. | 250/910 X |

FOREIGN PATENT DOCUMENTS

WO91/15762  10/1991  WIPO.
WO93/24823  12/1993  WIPO.

OTHER PUBLICATIONS

Plugge et al., J. of Pharm. & Biomed. Anal., vol. 11, No. 6, pp. 435–442 (1993).

Primary Examiner—Carolyn E. Fields
Assistant Examiner—Edward J. Glick
Attorney, Agent, or Firm—Francis P. Bigley; Mark R. Daniel

[57] ABSTRACT

A method and system for determining the homogeneity of one or more components of a mixture of ingredients, especially, is presented. Most importantly, it can be used to determine homogeneity of a tabletted mixture of the produced pharmaceuticals, including active and inactive ingredients. The method and system monitor the pharmaceutical material during tablet manufacture as a powder mix, granular mix and compressed tablets. This system uses near infrared technology for analyzing the uniformity and mass balance of the pharmaceutical mixture to control the tablet manufacturing process. As part of the system and method, a NIR spectral library, consisting of a pharmaceutical materials spanning the normal process range for is developed. Assessment of uniformity is accomplished by comparison of future production with the library of acceptable material.

1 Claim, 5 Drawing Sheets

- $RI = \dfrac{\text{SAMPLE ABS.} - \text{LIBRARY AVG. ABS.}}{\text{LIBRARY STANDARD DEVIATION (ABS.)}}$

- INCLUDES BOTH PROCESS AND MEASUREMENT VARIATION

- $\Delta RI = RI_{MAX} - RI_{MIN}$ AT EACH DATA CHANNEL

FIG. 1

METHOD AND SYSTEM FOR DETERMINING THE HOMOGENEITY OF TABLETS

BACKGROUND OF THE INVENTION

I. Field of the Invention

The present invention relates to the determination of the homogeneity of one or more components of a mixture of powdered ingredients especially pharmaceuticals, and most importantly, the tabletted mixture of the powdered pharmaceutical mixture, including active and inactive ingredients. This invention is generally classified in USPTO Class 250, subclasses 343 and 339.12.

II. Description of the Prior Art

U.S. Pat. No. 4,640,614 to Roberts et al., issued Feb. 3, 1987, disclose a method and apparatus for testing of particulate material, particularly food products or the like. This patent uses near infrared reflectance spectrometry for analyzing the particulate material. With reference to FIG. 1, the apparatus analyzes a sample, either compacted or uncompacted, for a property such as protein, fat content, moisture and color, see column 1, line 13. However, there is no teaching or suggestion of a continuous sampling technique, using a library as a reference for sample materials or testing a mixture of products for homogeneity or purity.

U.S. Pat. No. 2,650,307 to Koppius issued Aug. 25, 1953, discloses an infrared analyzer for detecting a mixture of chemical compounds, particularly gaseous compounds. With reference to FIG. 1, the gaseous compounds are distilled in the column 11 and analyzed by an infrared analyzer using windows in the distillation column.

U.S. Pat. Nos. 5,187,368 to Galante et al., issued Feb. 16, 1993 and 4,975,581 to Robinson et al., issued Dec. 4, 1990 are concerned with infrared analyses of liquids such as biological fluids or drug products in sealed bags or vials. In the Galante et al., patent, the sensed near-infrared spectra is compared with a known spectra for product evaluation. The Robinson et al., patent also uses a model to facilitate analysis of the biological fluid sample. Neither of these patents are concerned with particulate material, granulates or mixtures and mixture homogeneity.

U.S. Pat, No. 5,305,076 to Inoue et al., issued Apr. 19, 1994, discloses a method and apparatus to determine the constituent ingredients in a sample using infrared methods. The teachings of this patent are particularly adapted for sample gases such as those in a vehicle exhaust, see column 2, lines 20–23. Ceilings or limit values are calculated and compared to the sensed value for sample analyses.

U.S. Pat. No. 5,233,715 to Taylor issued Jun. 29, 1993, discloses a process for obtaining spectral information and quantifying physical properties of a sample. This patent is also especially adapted for analyses of gases as demonstrated by the examples beginning in column 24. In this patent, a reference channel is used for sample analyses in conjunction with the sensed sample values.

Finally, U.S. Pat. No. 5,099,123 to Harjunmaa issued Mar. 24, 1992, discloses a method and apparatus for non-invasive testing of body fluids and tissues. In this patent, a zero baseline is derived from a patient to be tested for use in analyzing the body fluids or tissue. Near infrared radiation is used for sample analysis.

In summary, the prior an discussed above teaches that is it well known to use near infrared radiation to analyze various types of materials for their properties and/or concentrations. The Roberts et al., patent is particularly adapted for testing particulate material. However, this patent uses a static testing method and is not concerned with analyzing a mixture of particular materials, either prior to or after the mixture is compacted into a tablet.

The prior an also teaches that it is known to compare sensed values using near-infrared spectra to a known value for sample evaluation, see for example, the Galante et al., patent. However, this prior an does not teach or fairly suggest the features of the invention as described above, for example, measuring mixture homogeneity or purity using near-infrared radiation, particularly in a continuous fashion for tablet evaluation.

SUMMARY OF THE INVENTION

I. General Statement of the Invention

According to the present invention; continuous monitoring of product uniformity can be accomplished using near infrared (NIR) spectroscopy, while meeting the requirements of being non-destructive and quantitative.

Modem tableting processes rely on mixing efficiency to obtain uniformity and proper active dose levels. Redundant systems monitor front end weight addition of various components to help assure proper formula ratios. Purity of components is determined assuming mass balance, an analytical assessment of total uniformity implies correct ingredient ratios and target dose.

Current compendial dose uniformity testing analyzes only active uniformity of the dosage form, usually a tablet.

By contrast, NIR analysis of tablet granulation uniformity is a more "accurate assessment" of overall process capability because the method generates information from all of the components in the tablet or tablet blend. A tableting process which is not efficiently blended will not produce consistent NIR spectral images.

In summary, this invention uses NIP, energy to generate a process photograph depicting the historical variation of an acceptable process. Spectral features arise from the interplay of vibrational quantum levels and optical phenomenon associated with a mixture of ingredients. Both inter-molecular and intra-molecular nearest neighbor events give rise to an image. New granulation consisting of several excipients plus active will generate a unique fingerprint which must be within historical variation. An additional advantage of this invention is that the technique can be used to determine priority of the starting materials and the blended mix as well as the final tablet.

While the prior art broadly teaches the use of near infrared sensing techniques to determine concentrations in a sample, it does not appear to teach or suggest the features of the invention including monitoring a mixture of materials including a pharmaceutical for material concentrations and mixture uniformity, utilizing the near infrared sensed values for control of a continuous tablet manufacturing process, generating a library of known values for comparison purposes with sensed values and using the sensed values to infer homogeneity and/or purity of the tablets without individual testing thereof.

II. Utility of the Invention

The present invention, as described above, can be utilized for the production of most pharmaceuticals, preferably for tableting or pelleting. Governmental and public safety require absolute assurance of accuracy in dosages of pharmaceutical medication, and any blending operation seeks to achieve Complete homogeneity. This invention provides the method and system for achieving this goal.

BRIEF DESCRIPTION OF THE DRAWINGS

FIG. 1 is the equation of "Recognition Index", typically known as a statistical "t-score or z-score" calculation. This function is capable of taking any data set and normalizing it to be centered around a "0" mean and scaled to have a standard deviation of "1". There are, in effect, numerous normal distributions calculated across the NIR spectrum. These are used to establish the acceptable limits for process variability.

Referring to FIG. 5, the near IR (NIR) source 1 is capable of generating NIR light, preferably between 1100–2500 nm with sufficient power to interrogate a representative sample volume either in transmission or reflectance modes. The light source 1 directs a beam down the light path 2. The light beam next enters an entrance slit 3 and is reflected from a minor 4 to a diffraction grating 5. The light refracted from the grating is sent along beam path 6 through a sorting filter 7 to assume the NIP, bright beam of 1100–2500 nm. After leaving through exit 8, the NIR beam 9 can be concentrated through lens 10, and then directed to the sample area 20. Sample 11 can be a solid tablet, in which case the reflected light 14 is detected at the reflectance detectors 12. An array of 4–8 NIR reflectance detectors, preferably six of PbS, which are commercially available, are sited at 45° angle to the light incident on the sample 11 to reduce the effect of specular, or stray energy reaching the detectors. The NIR spectrum generated is captured and stored in the detection amplifier 15.

DESCRIPTION OF THE PREFERRED EMBODIMENTS

Procedural Summary and Theory

Building a Library

Figure 2:
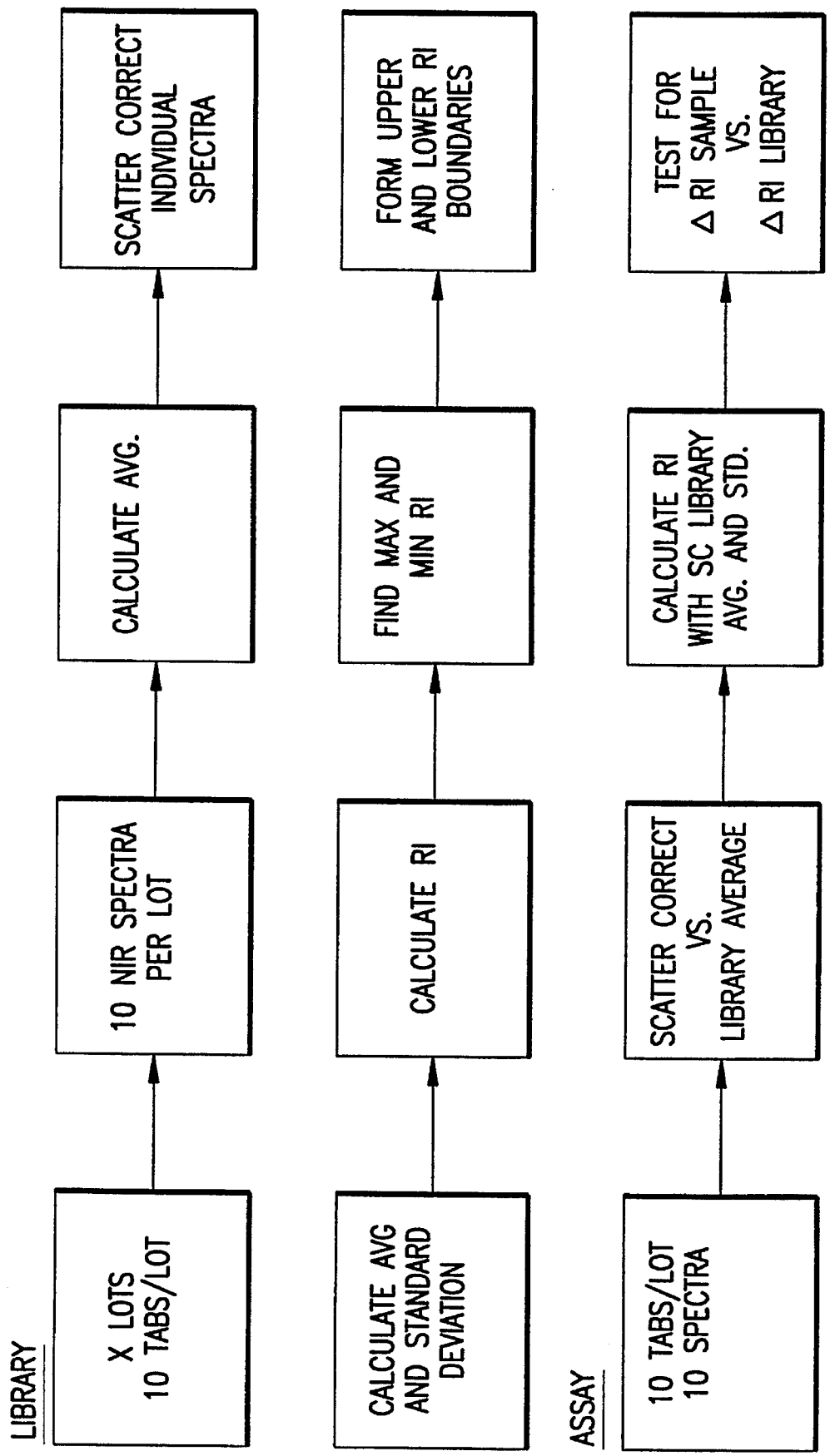
FIG. 2 is the RI/ΔRI calculation algorithm. Software has been developed which automates the various steps described. The calculation requires that a sufficient number of spectra from samples of interest be produced, so that the upper & lower limits of the recognition index may be pre-determined. Thereafter, the sample material is measured and compared to the library in a statistically significant calculation. There are Lotus and Excel spreadsheets capable of performing many of the above steps, which are normally accepted mathematical manipulations.
Figure 3:
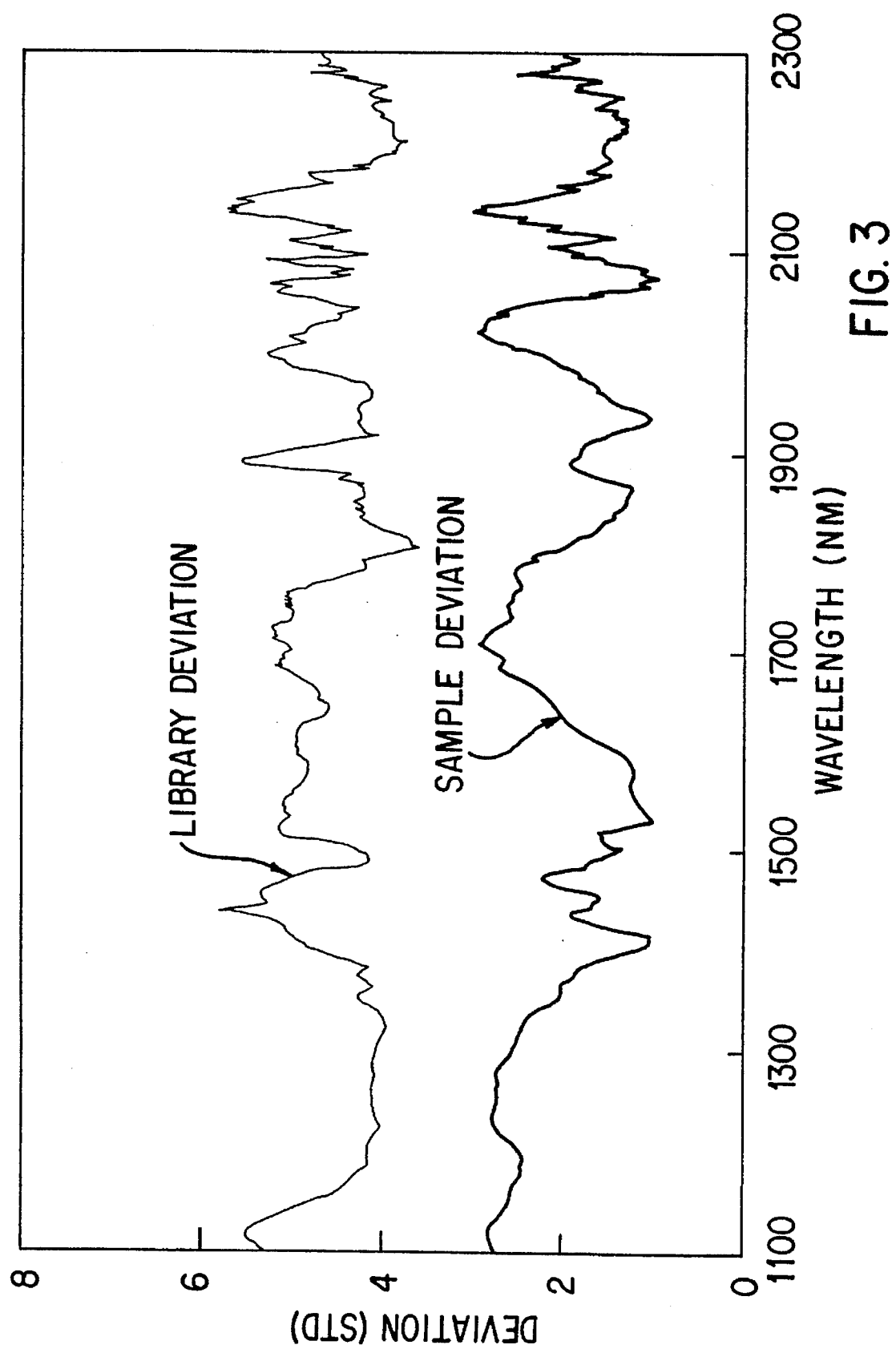
FIG. 3 shows the ΔRI limits for tablet processing. This is an instrument screen an operator would see after having run a new sample which has met the limits for acceptance across the spectrum. The deviation chart in FIG. 3 is a control chart whose x-axis depicts more than one independent variable. Certain areas of the spectrum can be isolated which correlate to chemical species of interest. Spectra regions have been correlated to active concentration, uniformity, water content, and particle size for pure bulk compounds, mixtures, and tablets. The mixtures can include any number of components; usually pharmaceuticals employ as few as 2 and up to 6 or more.
Figure 4:
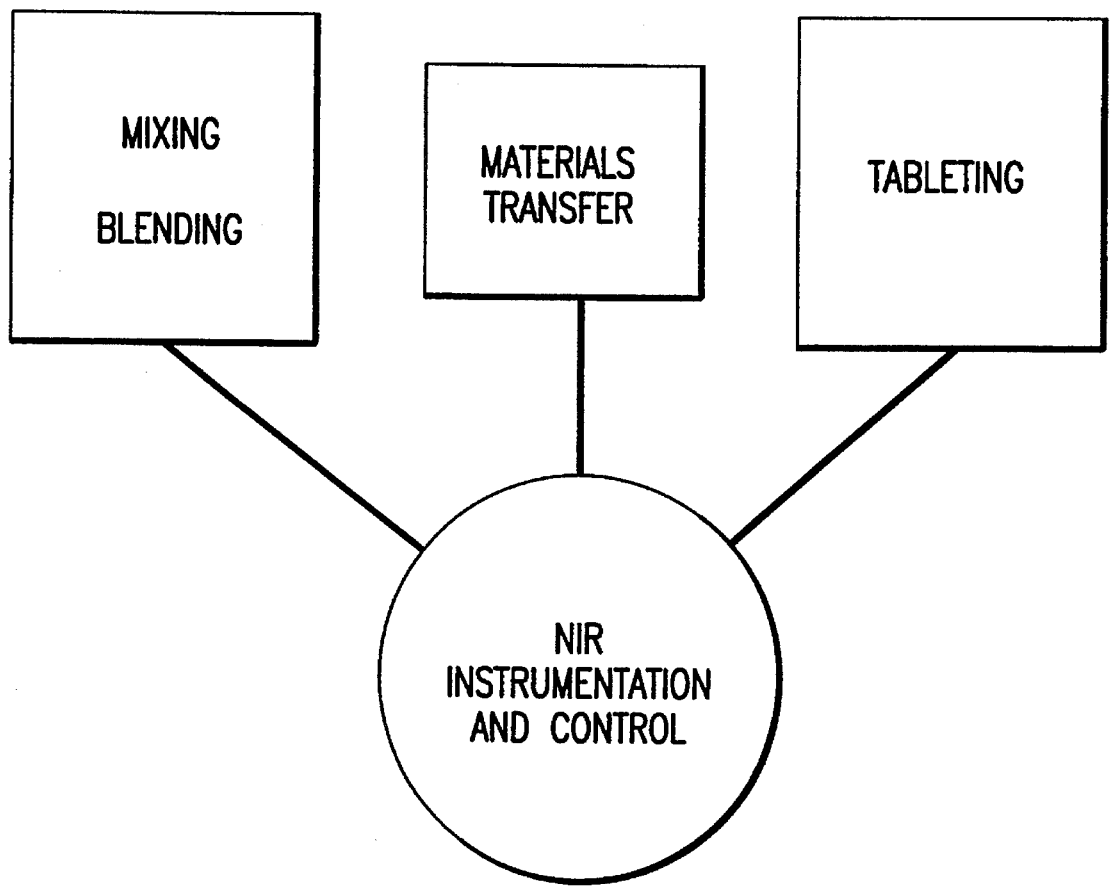
FIG. 4 is a schematic diagram of a control system using the NIR techniques of the present invention to control a pharmaceutical binding operation to achieve homogeneity.
Figure 5:
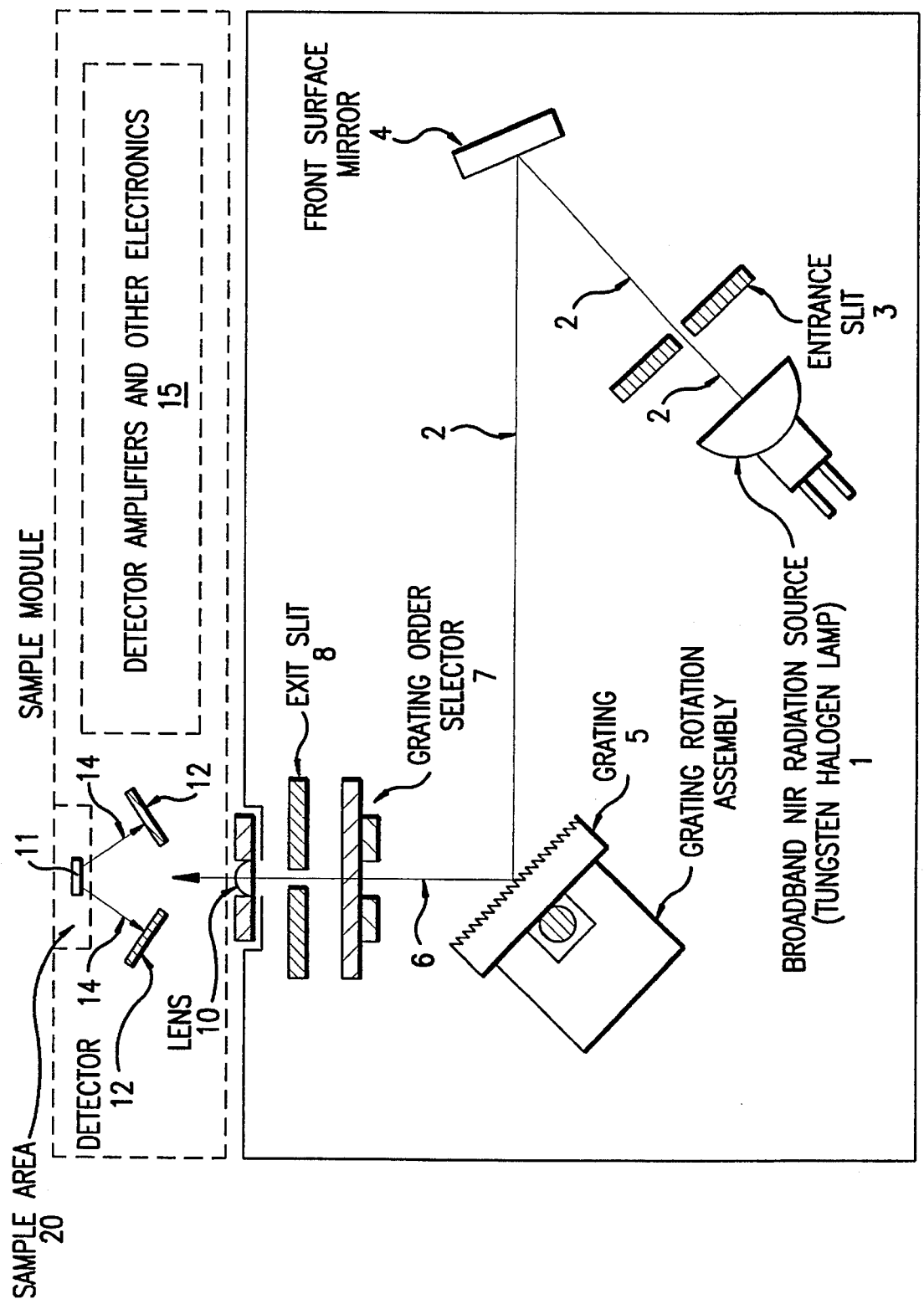
FIG. 5 is a schematic diagram of the apparatus set up for the present invention.

A sample (tablets or solid mixture of known acceptable quality) is scanned by the NIR spectrometer. These raw spectra are then preprocessed to correct for light scatter which can cause baseline offset. This phenomena must be corrected to obtain meaningful correlation of wavelength to parameters of interest. A software program which uses a multiplicative scatter correction algorithm has been developed. If not corrected, variation in offsets can dominate variations in the parameter of interest.

For the spectral dataset that will be used to build an RI library, let $x_1 \ldots x_k$ be the spectral values of a sample in that dataset and $m_1 \ldots m_k$ be the mean spectral values of that library dataset. A slope and y-intercept are estimated for each sample using the mean spectral values of the library by determining the least squares fit over all the wavelength channels (1 Æk) of the following equation:

$$x_k = b + a * m_k + e_k$$

In this equation, b is the y-intercept, a is the slope, and $e_k$ is the error for the regression fit. To obtain the scatter corrected spectrum for that sample, each original spectral data point first has the y-intercept subtracted and then the result is divided by the slope [see "The Effect of Multiplicative Scatter Correction (MSC) and Linearity Improvement in NIR Spectroscopy", T. Isaksson and T. Naes, Appl. Spectrosc. 42(7), 1273–1284 (1988)]:

$$x_k, \text{corrected} = (x_k, \text{original} - b)/a$$

The mean spectral values of the library dataset are saved for subsequent use in finding the slope (a) and y-intercept (b), the maximum and minimum RI, and ΔRI for each spectrum both library and test samples, described below.

Once data has been scatter corrected, the library spectra are subjected to the Recognition Index (RI) calculation at each data point (channel) across the NIR spectrum. This calculation is a means to determine the range of variability (uniformity) about the set-point of the pharmaceutical process. Data is mean centered and scaled to have a standard deviation of one according to the following equation:

$$RI_k = (x_k, \text{unknown} - m_k)/sd_k$$

x=individual absorbance values for each spectra m=mean absorbance of library spectra SD=standard deviation of library spectra k=channel or wavelength index The range of acceptable variability (ΔRI) for the library is calculated as follows:

$$\Delta RI_k = RI_{max} - RI_{min}$$

Library ΔRI values represent the absolute "historical" variability around a mean from an acceptable process.

Sample Analysis

Samples are scanned by the NIR spectrometer and scatter corrected in the same manner as library samples. Spectra are then analyzed by the RI and ΔRI equations (see above) to assess concentration uniformity. If the samples are tablets then weight variation must be gravimetrically determined. NIR analysis can not determine weight uniformity.

EXAMPLE

An example of the detailed method of sample analysis follows.

A representative sample of a minimum of ten tablets is obtained from a product to be tested.

After instrument diagnostics and stability have been evaluated, acquisition of NIR spectral data for individual tablets proceeds. Each tablet is positioned in the sample area using a tablet position die which minimizes variation in placement error. Care is taken to maintain a consistent orientation in the die so that the same tablet face is subjected to NIR analysis. For example, for engraved or embossed tablets, the engraving or embossing is always in the same orientation. The tablet positioning die is removed before the NIR spectrum is acquired. Spectra are taken and stored for RI/$\Delta$RI evaluation.

Samples are deemed uniform if the measured variation is within the historical variation determined by the library $\Delta$RI and/or weight measurement.

Once an RI/$\Delta$RI library is established for a specific product and dosage, it should be maintained as the standard. A new library should be established only in for the following situations:

1. instrument changes, such as servicing or upgrades
2. manufacturing process changes which invalidate the current library
3. repeated non-conforming/$\Delta$RI results which are not verified by compendial analysis.

As another embodiment of this invention, the wave-length of the beam directed at the sample can be broadened to include visible light, particularly for purity determinations of raw materials, many of which are essentially transparent to NIR. Other embodiments include a reflectance detectory probe for powders so that blended pharmaceutical mixtures can be monitored for homogeneity.

What is claimed is:

1. A process for measuring the uniformity of a pharmaceutical tableting process, comprising the steps of: selecting representative samples of tablets during the tableting process; placing each tablet within a tablet position die; removing the tablet position die; determining the near infrared spectrum of each tablet; and comparing the near infrared spectrum of each tablet to a previously generated "Recognition Index," of acceptable tabletted material; and determining which of the tablets are acceptable based on agreement with the "Recognition Index".

* * * * *